United States Patent [19]

Tendick, Sr.

[11] Patent Number: 4,892,711
[45] Date of Patent: Jan. 9, 1990

[54] FRAGRANCE DISPENSING DEVICE

[75] Inventor: Donald W. Tendick, Sr., Wauwatosa, Wis.

[73] Assignee: Lamplight Farms, Inc., Wauwatosa, Wis.

[21] Appl. No.: 139,909

[22] Filed: Dec. 31, 1987

[51] Int. Cl.<sup>4</sup> ............................................. A61L 9/02
[52] U.S. Cl. .................................... 422/125; 422/306; 422/4; 239/54
[58] Field of Search ....................... 422/4, 5, 125, 126, 422/305, 306; 239/34, 44, 51.5, 54, 55, 56, 60; 512/1, 2, 3, 4; 428/905; 431/288, 289

[56] References Cited

U.S. PATENT DOCUMENTS

| | | | |
|---|---|---|---|
| 1,817,057 | 8/1931 | Berry | 422/125 |
| 2,254,906 | 9/1941 | Petrulis | 21/117 |
| 3,567,119 | 3/1971 | Wilbert et al. | 239/60 |
| 3,819,342 | 6/1974 | Gunderman et al. | 431/288 |
| 3,895,928 | 7/1975 | Moran | 21/74 |
| 3,898,039 | 8/1975 | Lin | 422/125 |
| 3,958,917 | 5/1976 | Naz | 422/126 |
| 3,994,439 | 11/1976 | Van Breen et al. | 239/54 |
| 4,051,159 | 9/1977 | Tsoucalas et al. | 239/60 |
| 4,493,011 | 1/1985 | Spector | 239/56 |
| 4,647,428 | 3/1987 | Gyulay | 422/4 |
| 4,715,536 | 12/1987 | Capizzi et al. | 239/54 |
| 4,781,895 | 11/1988 | Spector | 422/125 |

FOREIGN PATENT DOCUMENTS 748994 12/1952 United Kingdom .................... 81/1

Primary Examiner—David L. Lacey
Assistant Examiner—Gregory R. Muir
Attorney, Agent, or Firm—Michael, Best & Friedrich

[57] ABSTRACT

A fragrance dispensing device includes an annular element made from a solid, synthetic, polymeric, plastic material, such as a low density polyethylene, containing about 5 to about 20 weight % of a vaporizable fragrance material uniformly dispersed throughout. In one embodiment, the element is mounted on an oil lamp and closely surrounds, but is maintained out of contact with, the burner assembly. When the wick is lit, heat from the burner vaporizes and drives the fragrance material from the plastic material.

11 Claims, 1 Drawing Sheet

U.S. Patent
Jan. 9, 1990
4,892,711
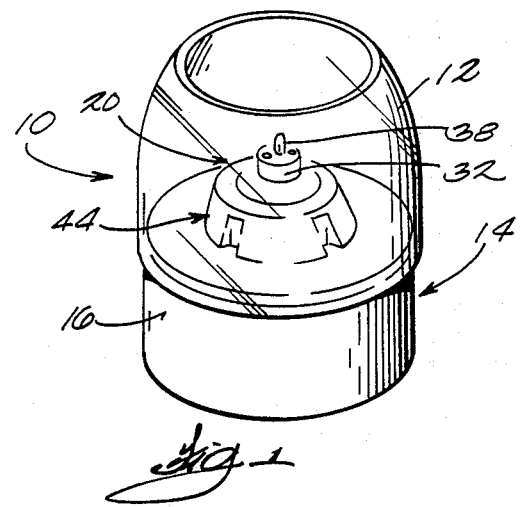
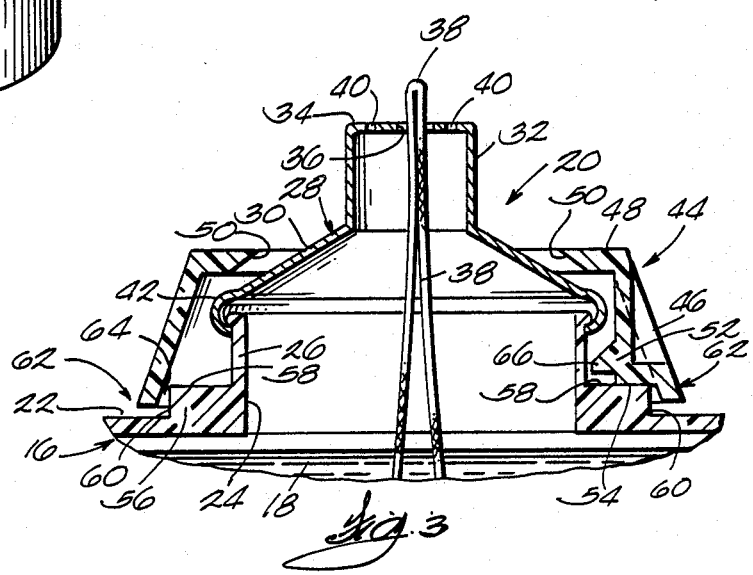

FRAGRANCE DISPENSING DEVICE

BACKGROUND OF THE INVENTION

The invention relates to devices for dispensing fragrances into the atmosphere and, in one aspect, to fluid burning lamps including such a device.

In one type of fragrance dispensing device, a reservoir or carrier containing a fragrance oil or the like is mounted in close proximity to a heat source, such as the burner of a fluid burning lamp, an electric light bulb, a candle, a heating element or the like. Example of prior fragrance dispensing device employing a reservoir or carrier which contains or supports a fragrance material and is located in surrounding relationship to the heat source are disclosed in Petrulis U.S. Pat. No. 2,254,906, Gyulay U.S. Pat. No. 4,647,428 and British Patent No. 748,994. Moran U.S. Pat. No. 3,895,928 discloses the use of two solid cakes of refractory material containing perfume oil or essence adjacent the opposite ends of an electrical heating element.

These devices have one or more shortcomings, such as being relatively expensive to manufacture, the fragrance is completely dispensed within a relatively short time period or is initially dispensed at a high rate and then quite slowly, or the fragrance dispensing element is not adaptable for use with a fluid burning lamp.

SUMMARY OF THE INVENTION

An object of the invention is to provide an inexpensive, effective fragrance dispensing element which can be used with a variety of different heat sources.

Another object of the invention is to provide a fluid burning lamp including an inexpensive, fragrance dispensing element. lamp including a disposble fuel cartridge and a fragrance dispensing element which dispenses fragrance throughout the life of the fuel cartridge.

A still further object of the invention is to provide a fluid burning lamp including a fragrance dispensing element which is arranged to insure that it never contacts any hot part even though the lamp is tipped over.

Other objects, aspects and advantages of the invention will become apparent upon reviewing the following detailed description, the drawing and the appended claims.

The invention provides a fragrance dispensing element which is adaptable for use with a fluid burning lamp, an electrical heating element, light bulb or similar heat source. The element has an annular shape and is made from a solid, synthetic, polymeric, plastic material containing about 5 to about 20 weight % of a vaporizable fragrance material uniformly dispersed throughout. The element is arranged to surround and be mounted in close proximity to, but out of contact with a heat source, such that the heat from the heat source vaporizes and drives the fragrance material from the plastic material.

The invention also provides a fluid burning lamp including a fluid containing canister, a burner assembly holding a wick and a fragrance dispensing element like that described above is mounted in close proximity to and out of contact with the burner assembly. When the wick is lit, heat from the burner assembly vaporizes and drives the fragrance material from the plastic material.

In one embodiment, the burner assembly includes a metal cap member which fits over a collar on the canister and has a central raised portion which holds the wick. The element has a ring-like shape, surrounds the cap member and is arranged to cooperate with the canister to prevent any part of the element contacting any part of the cap member. The element also is arranged to permit a free flow of air between the cap member and the element in order to produce a "chimney effect" which promotes dissemination of the fragrance material.

BRIEF DESCRIPTION OF DRAWING

FIG. 1 is a perspective view of an oil lamp embodying the invention.

FIG. 2 is an exploded, perspective view of the lamp illustrated in FIG. 1.

FIG. 3 is an enlarged sectional view of the burner assembly and fragrance dispensing element of the lamp illustrated in FIG. 1.

FIG. 4 is a bottom view of the fragrance dispensing element shown removed from the lamp.

DESCRIPTION OF THE PREFERRED EMBODIMENTS

The fragrance dispensing element of the invention can be used with a wide variety of heat sources including electric light bulbs, electrical heating elements, candles and the like. It is particularly adaptable for use with fluid burning lamps and will be described in connection with that application.

Illustrated in FIGS. 1 and 2 is a decorative lamp 10 including a chimney 12 which is removably mounted on a disposable fuel cartridge 14. The chimney 12 serves to dissipate light and can be transparent, translucent and/or colored and can have a smooth or textured surface to provide the desired aesthetic appearance and/or light transmission. The fuel cartridge 14 includes a canister 16 and a burner assembly 20. The canister 16 preferably is made from an inexpensive thermoplastic or thermosetting, synthetic, plastic material and is substantially filled with a suitable combustible fluid 18, such as a highly refined paraffin-based lamp oil. While the chimney 12 can be secured to the canister 16 by various suitable means, in a specific embodiment illustrated, it is held in place by frictional engagement.

Referring to FIG. 3, the canister 16 has a top wall 22 including a circular central opening 24 surrounded by an upstanding annular collar 26. The burner assembly 20 includes a cap member 28 having a frusto-conical section or hollow crown 30 and an upwardly extending, central cylindrical portion 32 having a cover 34. The cover 34 has a central opening 36 for receiving the upper portion of a wick 38 including a lower portion which extends into the combustible fluid 18. The cover 34 includes a pair of small openings 40 which serve as pressure relief ports.

The cap member 28 preferably is made from a metal and includes a peripheral flange which is crimped over the upper edge of the collar 26 to form an enlarged rim 42 and to secure the burner assembly 20 onto the canister 16.

Surrounding the burner assembly 20 is a fragrance dispensing element 44 made from a solid, synthetic, polymeric, plastic material containing a vaporizable perfume or fragrance material uniformly dispersed throughout. When the fragrance dispensing element 44 is subjected to heat emitted by a flame and the metal cap member 20 after the exposed portion of the wick 38 is lit, the fragrance material is vaporized and driven or released from the plastic material into the atmosphere.

The plastic material for the fragrance dispensing element should have a melting point high enough to prevent softening upon exposure to heat from the flame and the cap member 20 which can be in the order of about 100°–200° F. and even higher, depending upon the size of the burner assembly and the type of combustible fluid being used. The overall softening point of the element 44 decreases with increasing amounts of fragrance material, so this should be taken into consideration when selecting a plastic material for the element 44. The plastic material should not emit toxic flames in the event the element 44 accidentally contacts the flame and is burned.

Various suitable synthetic thermoplastic and thermosetting materials can be used. Thermoplastic materials such as polyethylene, polypropylene and ethylene-propylene copolymers presently are preferred, primarily because of their lower cost and ease of being formed into a variety of configurations. While high and medium density plastic materials can be used, low density materials generally provide a better release of the fragrance material and, therefore, are preferred.

The fragrance material used must be capable of being incorporated into and uniformly dispersed throughout the plastic material and then vaporize at a temperature produced by the flame and the cap member 20. Various natural and synthetic essential oils, perfumes and other conventional fragrance materials which are known to have these properties and to produce a desired odor, such as strawberry, rose, cinnamon, and the like, can be used. In most cases, the fragrance material will be a mixture of several ingredients.

When a thermoplastic material is used and the element is formed by injection molding, the fragrance material can be incorporated by thoroughly mixing with the molten thermoplastic material prior to the molding step. While the fragrance material can be admixed with the thermoplastic material in liquid form, pellets of a thermoplastic material containing approximately 25 weight % of a perfume and commercially available from polyvel, Hammonton, New Jersey, preferably are used. These pellets are admixed and melted along with the thermoplastic pellets making up the plastic material in the mixing chamber of an injection molding machine. When this approach is used, the thermoplastic of the fragrance pellets preferably is the same as that used for forming the plastic material.

The amount of fragrance material used should be sufficient for the element to continue releasing a noticeable fragrance throughout the life of the fuel cartridge, i.e., until the combustible fluid has been consumed. The active amount of fragrance material in the element 44 usually is about 10 to about 20 weight %, preferably about 10 to about 15 weight %. Amounts of fragrance material greater than about 20 weight % substantially increases the cost without a significant difference in the intensity of the fragrance released and also can reduce the softening point of the element 44 to an undesirable level. Amounts of fragrance material less than about 5 weight % generally do not provide a noticeable fragrance over an extended time period. For relatively small lamps using a highly refined, paraffin-based lamp oil, it has been found that the optimum active amount of a fragrance material in an element injected molded from a low density polyethylene is about 12.5 weight %.

In the specific embodiment illustrated, the element 44 is designed to cooperate with a canister 16 to prevent any contact with the flame or the metal cap member 28 and to insure a free flow of air between the element 44 and the cap member 28 during use. The element 44 has a ring-like shape and surrounds only the lower portion of the cap member 28. More specifically, the element 44 has an annular outer wall 46 having a frusto-conical shape and a top wall 48 extending radially inwardly from the top of the outer wall 46 and terminating in a central circular opening 50.

Extending radially inwardly from the inner surface of the outer wall 44 as a plurality (e.g., four) support members 52 circumferentially spaced at equal intervals and having a bottom edge 54. The canister top wall 22 includes a ledge 56 having an upper surface 58 extending radially outwardly from the collar 26 and a peripheral surface 60 depending from the top surface 58. The bottom edges 54 of the support members 52 rest on the ledge upper surface 58 to hold the element top wall 48 away from the crown 30 of the cap member 28 and to hold the lower edge of the element outer wall 44 away of the canister top wall 22. The top wall opening 50 preferably is tapered like the crown 30 to provide a uniform spacing between the crown 30 and the opening 50.

The lower portion 62 of the element outer wall 46 extends below the ledge upper surface 58 and is spaced outwardly from the ledge 56 to provide an opening 64 therebetween for a free flow of air. When the wick 38 is lit, the rising heat creates a "chimney effect" which promotes the flow of air over the inner and outer surfaces of the element 44 and enhances dissemination of the fragrance being released from the element 44. The opening 64 also serves as a drain for any combustible fluid or other liquid which might spill inside the element 44.

The spacing or opening 64 between the lower portion 62 of the element outer wall 46 and the ledge 56 is dimensioned so that, during radially inward movement of the element 44 toward the cap member 28, the inner surface of the lower portion 62 engages the ledge 56 and prevents any part of the element 44 from touching any part of the cap member 28.

Extending radially inwardly from each support member 52 is a projection 66. The projections 66 extend inwardly beyond the outer diameter of the cup member rim 42 and snap down over the rim 42 when the element 44 is installed. The projections 66 thereafter serve to prevent the element 44 from accidentally falling off or tipping over into contact with the cap member 28 in the event the lamp is tipped over or dropped.

The element 44 preferably is enclosed in a substantially air-tight package (not shown) prior to the time the lamp is first used in order to minimize premature release of the fragrance material. For use, the element 44 is removed from the package and installed over the burner assembly and the wick can be lit to dispense the fragrance material by lighting before or after the chimney 12 is installed on the fuel cartridge 14.

From the foregoing description, one skilled in the art can easily ascertain the essential characteristics of the invention and, without departing from the spirit and scope thereof, make various changes in modifications to adapt it to various usages.

I claim:

1. A fluid burning lamp comprising a canister containing a combustible fluid and having a top wall including an opening and an upstanding collar surrounding said opening;

a burner assembly mounted on said canister over said opening and including a wick having a lower portion which extends into the combustible fluid and an exposed upper portion which can be lit to provide a flame and further including a metal cap member which fits over said collar and has a central raised portion which holds the upper portion of said wick; and;

a ring-like fragrance dispensing element made from a solid, synthetic, polymeric, plastic material containing about 5 to about 20 weight % of a vaporizable fragrance material uniformly dispersed throughout and mounted on said canister and surrounding said burner assembly such that, when said wick is lit, heat from said burner vaporizes and drive said fragrance material from said plastic material, said element being arranged to cooperate with said canister to prevent contact of any part of said element with said cap member.

2. A lamp according to claim 1 wherein the amount of said fragrance material is about 10 to about 15 weight %.

3. A lamp according to claim 2 wherein an amount of said fragrance material is about 12.5 weight %.

4. A lamp according to claim 1 wherein said plastic material is a thermoplastic material.

5. A lamp according to claim 4 wherein said plastic material is a low density thermoplastic material.

6. A lamp according to claim 1 wherein said element is arranged to provide a passage for free flow of air between said cap member and said element when said wick is lit.

7. A lamp according to claim 6 wherein said element includes an outer wall spaced radially outwardly from said cap member and having a lower portion;

a plurality of circumferentially spaced support members extending radially inwardly from said outer wall and having a bottom edge which rests on a portion of said canister top wall and supports said element such that at least a substantial part of said outer wall is spaced away from said canister top wall.

8. A lamp according to claim 7 wherein said canister top wall includes a ledge having an upper surface extending radially outwardly from said collar and peripheral surface depending from said upper surface;

said bottom edges of said element support members rest on said edge upper surface; and said lower portion of said element outer wall extends below said ledge upper surface and is spaced outwardly therefrom such that, during radially inward movement of said element outer wall toward said cap member, said lower portion of said element outer wall engages said peripheral surface and prevents said element from contacting said cap member.

9. A lamp according to claim 8 wherein said cap member includes a radially outwardly extending rim having an outer diameter; and each of said support members includes a projection which extends radially inwardly beyond the outer diameter of said rim, said projections cooperating with said rim to resist lifting of said element away from said burner assembly.

10. A lamp according to claim 1 wherein said element includes an outer wall which is spaced radially outwardly from said cap member and has a lower portion and further includes a plurality of circumferentially spaced support members which extend radially inwardly from said outer wall and have a bottom edge;

said canister top wall includes a ledge having an upper surface extending radially outwardly from said collar and a peripheral surface depending from said upper surface;

said bottom edges of said support members rest on said ledge upper surface; and said lower portion of said element outer wall extends below said ledge upper surface and is spaced outwardly therefrom such that during radially inward movement of said element outer wall towards said cap member, said lower portion of said element outer wall engages said peripheral surface and prevents said element from contacting said cap member.

11. A lamp according to claim 1 wherein said element includes an outer wall which is spaced radially outwardly from said cap member and has a lower portion and further includes a plurality of circumferentially spaced support members which extend radially inwardly from said outer wall;

said cap member includes a radially outwardly extending rim having an outer diameter; and each of said support members includes a projection which extends radially inwardly beyond the outer diameter of said rim, said projections cooperating with said rim to resist lifting of said element away from said burner assembly.

* * * * *

UNITED STATES PATENT AND TRADEMARK OFFICE
CERTIFICATE OF CORRECTION

PATENT NO. : 4,892,711
DATED : January 9, 1990
INVENTOR(S) : Donald W. Tendick, Sr.

It is certified that error appears in the above-identified patent and that said Letters Patent is hereby corrected as shown below:

```
Column 1, line 36, the words "element. lamp" should read
---element.
     A further object of the invention is to provide such
a lamp---

Column 6, line 2, the word "edge" should read ---ledge---.
```

Signed and Sealed this

Eighth Day of January, 1991

Attest:

HARRY F. MANBECK, JR.

*Attesting Officer*     *Commissioner of Patents and Trademarks*